United States Patent [19]

Tahara et al.

[11] Patent Number: 5,028,603

[45] Date of Patent: Jul. 2, 1991

[54] ESTER-SUBSTITUTED THIENOTRIAZOLODIAZEPINE COMPOUNDS AND PHARMACEUTICAL USES THEREOF

[75] Inventors: Tetsuya Tahara; Minoru Moriwaki, both of Nakatsu; Masao Abe, Buzen; Michio Terasawa, Nakatsu, all of Japan

[73] Assignee: Yoshitomi Pharmaceutical Industries, Ltd., Osaka, Japan

[21] Appl. No.: 350,589

[22] PCT Filed: Jun. 6, 1988

[86] PCT No.: PCT/JP88/00547

§ 371 Date: Feb. 3, 1989

§ 102(e) Date: Feb. 3, 1989

[87] PCT Pub. No.: WO88/09792

PCT Pub. Date: Dec. 15, 1988

[30] Foreign Application Priority Data

Jun. 8, 1987 [JP] Japan ................. 62-142841

[51] Int. Cl.$^5$ .................. C07D 495/12; A61K 31/55
[52] U.S. Cl. .................................... 514/220; 540/560
[58] Field of Search ..................... 540/560; 514/220

[56] References Cited

U.S. PATENT DOCUMENTS 4,900,729  2/1990  Stransky et al. ................ 540/560

FOREIGN PATENT DOCUMENTS 0176927  4/1986  European Pat. Off. ......... 514/220

Primary Examiner—Mukund J. Shah
Assistant Examiner—Philip I. Datlow
Attorney, Agent, or Firm—Wenderoth, Lind & Ponack

[57] ABSTRACT

There are provided novel ester-substituted thieno-triazolodiazepines useful for the treatment of various PAF-induced diseases.

2 Claims, No Drawings

ESTER-SUBSTITUTED THIENOTRIAZOLODIAZEPINE COMPOUNDS AND PHARMACEUTICAL USES THEREOF

TECHNICAL FIELD

The present invention relates to novel and pharmaceutically useful ester substituted thienotriazolodiazepine compounds and pharmaceutically acceptable salts thereof, and pharmaceutical uses thereof.

BACKGROUND ART

Certain s-triazolo[3,4-c]thieno[2,3-e][1,4]diazepine compounds are known to exhibit useful pharmacological activities against the central nervous system such as antianxiety or anticonvulsant activities as disclosed in U.S. Pat. No. 3,904,641.

Japan. J. Pharmacol., vol. 44, p. 381-391 (1987) discloses that the similar type of the compounds exhibits antagonistic activity on platelet-activating factor (hereinunder also referred to as PAF), and further EP-A 194416 discloses that another type of the compounds having a carboxylic acid amide derivatives as the side chain exhibit antagonistic activity on PAF.

According to the elucidation of the structure of platelet-activating factor, its physiological roles have been investigated, and various PAF-induced inflammatory diseases such as allergic diseases, anaphylactic shocks, vascular diseases as DIC (disseminated intravascular coagulation syndrome), myocardial diseases, asthma, pulmonary edema and adult respiratory diseases have been known. The PAF-antagonistic compounds are considered to be very useful for the prevention and treatment of above-mentioned diseases. It is known that certain thienotriazolodiazepine compounds exhibit PAF-antagonist activity as mentioned above. However, such compounds are not sufficient in view of the separation from the effect on the central nervous system, the potency, the effectiveness by the oral administration or the duration of activity.

DISCLOSURE OF THE INVENTION

The present inventors have made intensive invenstigations in order to develop the compounds which have PAF-antagonistic activity and possess less central depressing effect such as sedative activity or muscle relaxation activity, and are effective by oral administration and long-lasting, and to provide useful compounds and medicines.

As a result, the present invetors have found that the thienotriazolodiazepine compounds substituted by an acyloxyalkyl group as a side chain at the 2-position exhibit potent PAF-antagonistic activity and accord with the target of the development as mentioned above, and completed the present invention.

Moreover, it is expected that the compounds, especially, wherein the acyl residue is carboxyl residue of the carboxylic acid compounds having a cyclooxygenase-inhibitory acid antiinflammatory activity produce metabolically the acid antiinflammatory compounds in vivo and are also effective against non-PAF-induced inflammatory models which are not sufficient in the potencies of the treatment based on only PAF-antagonistic activity.

Namely, the first present invention relates to provide ester-substituted thienotriazolodiazepine compounds of the formula:

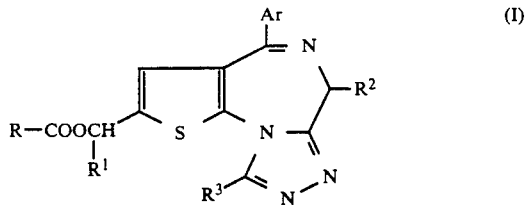

wherein Ar is pyridyl, phenyl or substituted phenyl by one to three substituents (wherein the substituents are the same or different and each is halogen, alkyl having 1 to 4 carbon atoms or alkoxy having 1 to 4 carbon atoms), $R^1$ and $R^3$ are the same or different and each is hydrogen or alkyl having 1 to 4 carbon atoms, $R^2$ is hydrogen, alkyl having 1 to 4 carbon atoms or trifluoromethyl, R is straight or branched chain alkyl having 1 to 18 carbon atoms, straight or branched chain alkenyl having 2 to 18 carbon atoms, aryl, substituted aryl by one to three substituents which are the same or different (wherein substituents are halogen, hydroxy, alkyl having 1 to 4 carbon atoms, alkoxy having 1 to 8 carbon atoms or aralkyloxy), aralkyl, substituted aralkyl by at least one substituent which is the same or different on aromatic ring or alkyl chain [wherein the substituent on the aromatic ring is halogen, hydroxy, alkyl having 1 to 4 carbon atoms, alkoxy having 1 to 8 carbon atoms, aralkyloxy, cycloalkyl, alkenyloxy having 2 to 4 carbon atoms, acyl, phenyl, pyridyl, phenoxy, phenylamino which may be substituted by one to three substituents (wherein the substituents are halogen, alkyl having 1 to 4 carbon atoms or alkoxy having 1 to 4 carbon atoms) or heterocyclic ring having nitrogen atoms, or the substituent on the alkyl chain is oxo or alkyl having 1 to 4 carbon atoms], fused aralkyl with the heterocyclic ring (wherein aryl, heterocyclic ring or alkyl chain may be substituted by a substituent), aralkenyl, substituted aralkenyl by one to three substituents on the aromatic ring (wherein the substituents on the aromatic ring are the same or different and each is hydroxy, alkyl having 1 to 4 carbon atoms or alkoxy having 1 to 4 carbon atoms), heteroarylalkyl (wherein the heteroaryl and the alkyl chain may be substituted by a substituent such as halogen, oxo, hydroxy, alkyl having 1 to 4 carbon atoms, alkoxy having 1 to 4 carbon atoms or benzoyl which may be substituted by substituents (wherein the substituents are halogen, alkyl having 1 to 4 carbon atoms or alkoxy having 1 to 4 carbon atoms)) or indenylalkyl which may be substituted by substituents (wherein the indenyl and the alkyl chain may be substituted by substituents such as halogen, oxo, hydroxy, alkyl having 1 to 4 carbon atoms, alkoxy having 1 to 4 carbon atoms or p-(methylsulfinyl)phenylmethylene), and pharmaceutically acceptable salts thereof.

Moreover, the second present invention relates to provide a pharmaceutical composition comprising estersubstituted thienotriazolodiazepine compounds of the abovementioned formula (I) or pharmaceutically acceptable salts thereof.

The symbols of the general formula (I) and each of the below-mentioned general formulae are defined in detail below.

Halogen means chlorine, bromine, fluorine or iodine; alkyl means alkyl having 1 to 4 carbon atoms such as methyl, ethyl, propyl, isopropyl, butyl, isobutyl or tert-butyl; alkoxy means alkoxy having 1 to 4 carbon atoms such as methoxy, ethoxy, propoxy, isopropoxy, butoxy, isobutoxy or tert-butoxy; straight and branched chain alkyl having 1 to 18 carbon atoms means methyl, ethyl, propyl, isopropyl, butyl, isobutyl, tert-butyl, pentyl, isopentyl, neopentyl, hexyl, heptyl, octyl, nonyl, decyl, undecyl, dodecyl tridecyl, tetradecyl, pentadecyl, hexadecyl, heptadecyl or octadecyl; straight and branched chain alkenyl having 2 to 18 carbon atoms means vinyl, allyl, isopropenyl, 1-butenyl, 2-butenyl, 2-pentenyl, 2-hexenyl, geranyl or 8,11-heptadecadienyl; aryl means phenyl or naphthyl; alkoxy means alkoxy having 1 to 8 carbon atoms such as methoxy, ethoxy, propoxy, isopropoxy, butoxy, tert-butoxy, pentyloxy, heptyloxy or octyloxy; aralkyloxy means benzyloxy, 2-phenylethyloxy, 3-phenylpropyloxy or 4-phenylbutyloxy; aralkyl means benzyl, phenylethyl, phenylpropyl; phenylbutyl, naphthylmethyl, naphthylethyl or naphthylbutyl; cycloalkyl means cycloalkyl having 3 to 7 carbon atoms such as cyclopropyl, cyclobutyl, cyclopentyl cyclohexyl or cycloheptyl; alkenyloxy means alkenyloxy having 2 to 4 carbon atoms such as vinyloxy, allyloxy, propenyloxy or butenyloxy; acyl means acetyl, propionyl, butylyl, pivaloyl or benzoyl; heterocyclic ring having nitrogen atoms means 5 to 6-membered heterocyclic ring (which may contain unsaturated bonds) having a nitrogen, such as 3-pyrrolin-1-yl, 1-pyrolidinyl, piperidino, 1-pyrrolyl or 1-imidazolyl; aralkyl fused with heterocyclic ring means (phenothiazin-1-yl)methyl, (phenothiazin-2-yl)methyl, 1-(benzopyrano[2,3b]pyridin-6-yl)ethyl, 1-(benzopyrano[2,3-b]pyridin-7-yl)ethyl, 1-(carbazol-1-yl)ethyl, 1-(carbazol-2-yl)ethyl, 1-(benzothiazol-4-yl)ethyl or 1-(benzothiazol-5-yl)ethyl; aralkenyl means styryl or cinnamyl; heteroaryl means indol-2-yl, indol-3-yl, 2-pyrrolyl, 3-pyrrolyl, 2-thienyl or 3-thienyl; indenylalkyl means 2-indenylmethyl or 3-indenyl-methyl. The alkyl chain of aralkyl and heteroarylalkyl is preferably alkyl having 1 to 4 carbon atoms.

Further, the R moiety in the above mentioned compounds of formula (I) includes the carboxyl residue of antiinflammatory carboxylic acid compounds such as ibuprofen, indomethacin, flurbiprofen, fenoprofen, pirprofen, metiazinic acid, pranoprofen profen, carprofen, naproxen, diclofenac, alclofenac, ketoprofen, tolmetin, fenbufen, sulindac, tiaprofen, tazeprofen, hexaprofen or 2-(4-(2-pyridylamino)phenyl)propionic acid (AD-1491), and, in more detail, is illustrated 1-(4-iso-butylphenyl)ethyl, [1-(4-chlorobenzoyl)-5-methoxy-2-methylindol-3-yl]methyl, 1-(2-fluoro-4-biphenylyl)ethyl, 1-(3-phenoxyphenyl)ethyl, 1[3-chloro-4-(3-pyrrolin-1-yl)phenyl]ethyl (10-methylpheno-thiazin-2-yl)methyl, 1-(5H-[1]benzopyrano[2,3-b]pyridin-7-yl)ethyl, 1-(6-chlorocarbazol-2-yl)ethyl, 1-(6-methoxy-2-naphthyl)ethyl, 2-(2,6-dichlorophenylamino)benzyl, 4-allyloxy-3-chlorobenzyl, 1-(3-benzoylphenyl)ethyl, 1-methyl-5-(4-methylbenzoyl)-2-pyrrolylmethyl, 2-(4-biphenylyl-carbonyl)ethyl, 5-fluoro-2-methyl-1-{[p-(methylsulfinyl)phenyl]methylene}-1H-3-indenylmethyl, 1-(5-benzoyl-2-thienyl)ethyl, 1-(2-phenyl-benzothiazol-5-yl)ethyl, 1-(4-cyclohexylphenyl)ethyl or 1-[4-(2-pyridylamino)phenyl]ethyl.

The pharmaceutically acceptable salts of the compounds of formula (I) include salts with an inorganic acid such as hydrochloric acid, sulfuric acid, phosphoric acid, hydrobromic acid, nitric acid and so on, and an organic acid such as maleic acid, fumaric acid, malic acid, tartaric acid, succinic acid, citric acid, acetic acid, lactic acid, methanesulfonic acid, p-toluenesulfonic acid, pamoic acid and so on.

If the compounds of the present invention contain asymmetric carbon atoms, the present invention includes all classes of optical isomers or diastereoisomers on the basis of the asymmetric carbon atom(s) and the mixture thereof. Moreover, the present invention also embraces the corresponding position isomers.

The compounds of formula (I) of the present invention can, for example, be prepared by the following methods:

The compounds of the formula (I) can be prepared by reacting an alcohol compound of the formula:

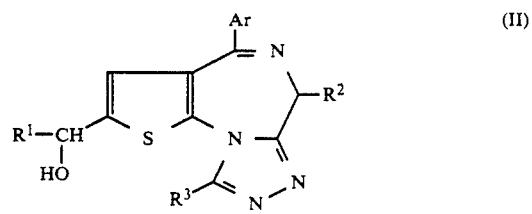

wherein each symbol is as defined above, with a carboxylic acid compound of the formula:

wherein R is as defined above, and the derivative thereof (e.g. acid halide, acid anhydride or mixed acid anhydride).

The compounds of formula (III) represented by R—COOH include the antiinflammatory carboxylic acid compounds such as ibuprofen, indomethacin, flurbiprofen, fenoprofen, pirprofen, metiazinic acid, pranoprofen, carprofen, naproxen, diclofenac, alclofenac, ketoprofen, tolmetin, fenbufen, sulindac, tiaprofen, tazeprofen, hexaprofen or 2-(4-(2-pyridylamino)phenyl)propionic acid (AD-1491).

The reaction is preferably carried out at 0° C. to a reflux temperature of the solvent for 1 to 24 hours in the presence of an acid scavenger such as an organic base (e.g. triethylamine, pyridine or dimethylaniline) or an inorganic base (e.g. sodium hydrogencarbonate, potassium carbonate, sodium carbonate, potassium hydroxide or sodium hydroxide) in a suitable solvent (e.g. pyridine, dimethylaniline, benzene, toluene, xylene, tetrahydrofuran, dioxane, chloroform, methylene chloride or a mixture thereof).

The compounds of formula (I) obtained by the abovementioned method can be separated and purified from the reaction mixture by the per se known method such as recrystallization and chromatography.

The compounds of formula (I) can be converted into the pharmaceutically acceptable salts as mentioned above by treating with an inorganic acid or an organic acid in a conventional method.

The preferable compounds of formula (I) are the compound consisting of 4-(2-chlorophenyl)-2-(1-(4-methoxybenzoyl)oxyethyl)-9-methyl-6H-thieno [3,2-f][1,2,4]triazolo[4,3-a][1,4]diazepine 2-(1-(2-(4-isobutylphenyl)propionyl)oxyethyl)-4-(2-chlorophenyl)-9-methyl-6H-thieno [3,2-f][1,2,4]triazolo[4,3a][1,4]diazepine 2-(1-(2-(4-isobutylphenyl)propionyl)oxyethyl)-4-(2-methoxyphenyl)-9-methyl-6H-thieno [3,2-f][1,2,4]triazolo[4,3-a][1,4]diazepine 2-(1-(2-(4-isobutylphenyl)propionyl)oxyethyl)-4-(2-methylphenyl)-9-methyl-6H-thieno[3,2-f][1,2,4]triazolo[4,3a][1,4]diazepine 2-(1-(4-chlorobenzoyl)oxyethyl)-4-(2-methylphenyl)-9-methyl-6H-thieno[3,2-f][1,2,4]triazolo[4,3-a][1,4]diazepine 2-(1-(4-chlorobenzoyl)oxyethyl)-4-(2-chlorophenyl)-9-methyl-6H-thieno[3,2-f][1,2,4]triazolo[4,3-a][1,4]diazepine 2-(1-(2-phenylpropionyl)oxyethyl-4-(2-chlorophenyl)-9-methyl-6H-thieno[3,2-f][1,2,4]triazolo[4,3-a][1,4]diazepine 2-(1-cinnamoyloxyethyl)-4-(2-chlorophenyl)-9-methyl-6H-thieno[3,2-f][1,2,4]triazolo[4,3-a][1,4]diazepine 4-(2-chlorophenyl)-2-(1-tridecanoyloxyethyl)-9-methyl-6H-thieno[3,2-f][1,2,4]triazolo[4,3-a][1,4]diazepine 4-(2-chlorophenyl)-9-methyl-2-(1-(4-octylbenzoyl)oxyethyl)6H-thieno[3,2-f][1,2,4]triazolo[4,3-a][1,4]diazepine 4-(2-chlorophenyl)-9-methyl-2-(1-(4-(4-phenylbutyloxy)-benzoyl)oxyethyl)-6H-thieno[3,2-f][1,2,4]triazolo[4,3a][1,4]diazepine 2-(1-acetoxyethyl)-4-(2-chlorophenyl)-9-methyl-6H-thieno[3,2-f][1,2,4]triazolo [4,3-a][1,4]diazepine 2-(1-benzoyloxyethyl)-4-(2-chlorophenyl)-9-methyl-6H-thieno[3,2-f][1,2,4]triazolo[4,3-a][1,4]diazepine or 4-(2-chlorophenyl)-9-methyl-2-(1-pivaloyloxyethyl)-6H-thieno[3,2-f][1,2,4]triazolo[4,3-a][1,4]diazepine The obtained compounds of formla (I) and the pharmaceutically acceptable salts thereof exhibit PAF-antagonistic activity and are useful as PAF-antagonistic drugs. The diseases which can be treated include various PAF-induced diseases such as various inflammatory diseases, allergic diseases, anaphylactic shocks, myomuscular diseases, asthma, pulmonary edema or adult respiratory diseases. Especially, the compounds having a residue of cyclooxygenase inhibitoryacidic antiinflammatory drug in the acyl residue can be expected to be produced metabolically in vivo and are effective against non-PAF-induced inflammatory models which are not sufficient in the potencies of the treatment based on PAF-antagonistic activity alone.

Then, pharmacological effects of the compounds of the present invention are illustrated as follows:

Namely, PAF-antagonistic activity of the compounds of the present invention was determined by examining the antagonistic effects on PAF-induced platelet aggregation in rabbits in vitro.

Experiment 1: Inhibitory effect on platelet aggregation in rabbits (in vitro test)

Blood samples to which was added 1/10 volume of 3.8% sodium citrate solution were collected from rabbits. Platelet rich plasma (PRP) was prepared by centrifuging the blood sample at 200×g for 10 minutes, and platelet poor plasma (PPP) was prepared by centrifuging the remaining blood sample at 1000× g for 10 minutes.

Aggregation ability was measured with a turbidimetric device (6-channel NKK Hematracer 1, model PAT-6A) according to the method of G.V.R. Born described in J. Physiology, vol. 168, p. 178 (1963). The aggregometer was adjusted in sensitivity to give light transmission values of 0 and 100% for PRP and PPP, respectively. With stirring at 1000 rpm, 0.3 μl of test compound solution or solvent was added to 0.3 ml of PRP. After the mixture was kept at 37° C. for 2 minutes, to the mixture was added 3 μl synthetic PAF at the final concentration of $1.8 \times 10^{-7}$ M and the light transmission was recorded for 5 minutes.

The inhibition percentage of test compounds on platelet aggregation was calculated from the following formula by measuring the maximal light transmission in the presence and absence of the test compounds.

$$\% \text{ of inhibition} = \left(1 - \frac{\text{maximal aggregation in the presence of the test compound}}{\text{maximal aggregation in the absence of the test compound}}\right) \times 100$$

$IC_{50}$ (μg/ml, concentration of 50% inhibition) was graphically determined. The results were summarized in Table 1.

TABLE 1

| Test compound (Example Number) | Inhibition of PAF-induced platelet aggregation $IC_{50}$(μg/ml) |
|---|---|
| 2 | 0.01–0.03 |
| 4 | 0.03–0.1 |
| 13 | 0.1–0.3 |
| 14 | 0.2 |
| Etizolam | 1.3 |

In Table 1, Etizolam is a general name of 6-(o-chlorophenyl)-8-ethyl-1-methyl-4H-s-triazolo [3,4c]thieno[2,3-e][1,4]diazepine.

According to the results of the above experiments, the compounds of the present invention exhibit potent PAF-antagonistic activity, and further, such activity is far more potent than that of Etizolam which was employed as a comparison compound.

Experiment 2: Acute toxicity

Acute toxicity of the compounds of the present invention was investigated in six male mice. The mice were observed for 5 days after oral administration of test compounds and all aminals servived at the dose 1000 mg/kg.

The compounds of formula (I) of the present invention and pharmaceutically acceptable salts thereof can be safely administered orally or parenterally in the form of tablets, pills, powder, capsules, granules, solutions, inhalants, suppositories, percutaneous absorption preparations or injectable solution which can be prepared by mixing a therapeutically effective amount of the compound with a pharmaceutically acceptable additives such as an excipient, an extender, a diluent or a solubilizer.

The dose may vary depending upon the compound selected, the severity of the diseases or the age, and the daily dose for human adults ranges from 0.1–100 mg in a single or multiple dose.

The present invention will be more concretely explained by the following examples, but they should not be thought to limit the scope of the invention.

EXAMPLE 1

To a solution of 2 g of 4-(2-chlorophenyl)-2-(1-hydroxyethyl)-9-methyl-6H-thieno[3,2-f][1,2,4]triazolo[4,3-a][1,4]diazepine dissolved in 20 ml of pyridine is added 1.1 g of 4-methoxybenzoyl chloride and then stirred under ice-cooling for 2 hours. After concentrating under reduced pressure, the residue is dissolved in 100 ml of ethyl acetate, the mixture is washed with 5% aqueous sodium hydrogencarbonate solution and sodium chloride solution, and dried over anhydrous magnesium sulfate. After filtering off, the filtrate is concentrated under reduced pressure. The oily residue is subjected to chromatography on silica gel and eluted with chloroform-methanol (100:1-100:2). The objective fraction is concentrated under reduced pressure and the residue is crystallized from ethyl acetate-hexane to give 0.4 g of 4-(2-chlorophenyl)-2-(1-(4-methoxybenzoyl)oxy) ethyl-9-methyl-6H-thieno[3,2-f][1,2,4]triazolo[4,3-a][1,4]diazepine as crystals, melting at 167°-170° C.

EXAMPLE 2

To a solution of 4 g of 4-(2-chlorophenyl)-2-(1-hydroxyethyl)-9-methyl-6H-thieno[3,2-f][1,2,4]triazolo[4,3-a][1,4]-diazepine dissolved in 40 ml of pyridine is added 3 g of 2-(4-isobutylphenyl)propionyl chloride under ice-cooling and then reacted for 2 hours. After completion of the reaction, the mixture is concentrated under reduced pressure and the residue is dissolved in 40 ml of ethyl acetate. The solution is washed with 5% aqueous sodium hydrogencarbonate solution and sodium chloride solution and dried over anhydrous magnesium sulfate. After filtering off, the filtrate is concentrated under reduced pressure and the oily residue is subjected to chromatography on silica gel and eluted with chloroform-methanol (100:1-100:2). The objective fraction is concentrated under reduced pressure to give 2-(1-(2-(4-iso-butylphenyl)propionyl) oxyethyl)-4-(2-chlorophenyl)-9-methyl-6H-thieno[3,2-f][1,2,4]triazolo[4,3-a][1,4]diazepine as an amorphous powder.

EXAMPLE 3

To a solution of 0.8 g of 2-(1-hydroxyethyl)-4-(2-methoxyphenyl)-9-methyl-6H-thieno[3,2-f][1,2,4]triazolo[4,3a][1,4]diazepine dissolved in 10 ml of pyridine is added 0.6 g of 2-(4-isobutylphenyl)propionyl chloride under ice-cooling and then stirred for 2.5 hours. After completion of the reaction, the mixture is concentrated under reduced pressure and the residue is dissolved in 20 ml of chloroform. The solution is washed with 5% aqueous sodium hydrogencarbonate solution and sodium chloride solution and dried over anhydrous magnesium sulfate. After filtering off, the filtrate is concentrated under reduced pressure, the oily residue is subjected to chromatography on silica gel and eluted with chloroform-methanol (100:1-100:2). The objective fraction is concentrated under reduced pressure to give 0.49 g of 2-(1(2-(4-isobutylphenyl) propionyl)oxy)ethyl-4-(2-methoxyphenyl)-9-methyl-6H-thieno[3,2-f][1,2,4]triazolo[4,3-a][1,4]diazepine as an amorphous powder.

EXAMPLE 4

To a solution of 1.3 g of 2-(1-hydroxyethyl)-4-(2-methyl-phenyl)-9-methyl-6H-thieno [3,2-f][1,2,4]triazolo[4,3-a][1,4]diazepine dissolved in 16 ml of pyridine is added 0.95 g of -(4-isobutylphenyl)propionyl chloride under ice-cooling and then stirred for 2 hours. After completion of the reaction, the mixture is concentrated under reduced pressure and the residue is dissolved in 50 ml of chloroform. The solution is washed with 5% aqueous sodium hydrogencarbonate solution and sodium chloride solution, and dried over anhydrous magnesium sulfate. After filtering off, the filtrate is concentrated under reduced pressure and the oily residue is subjected to chromatography on silica gel and eluted with chloroform-methanol (100:1-100:3). The objective fraction is concentrated under reduced pressure to give 1.3 g of 2-(1-(2-(4-isobutylphenyl)propionyl) oxyethyl)-4-(2-methylphenyl)-9-methyl-6H-thieno[3,2-f][1,2,4]triazolo[4,3-a][1,4]diazepine as an amorphous powder.

EXAMPLE 5

To a solution of 1.1 g of 2-(1-hydroxyethyl)-4-(2-methyl-phenyl)-9-methyl-6H-thieno [3,2-f][1,2,4]triazolo[4,3-a][1,4]diazepine dissolved in 14 ml of pyridine is added 0.63 g of 4-chlorobenzoyl chloride under ice-cooling and then stirred for 2.5 hours. After completion of the reaction, the mixture is concentrated under reduced pressure and the residue is dissolved in 50 ml of chloroform. The solution is washed with 5% aqueous sodium hydrogencarbonate solution and sodium chloride solution and dried over anhydrous magnesium sulfate. After filtering off, the filtrate is concentrated under reduced pressure and the residue is subjected to chromatography on silica gel and eluted with chloroform-methanol (100:1-100:3). The objective fraction is concentrated under reduced pressure to give 0.5 g of 2-(1-(4-chlorobenzoyl)oxyethyl)-4-(2-methylphenyl)-9-methyl-6H-thieno[3,2-f][1,2,4]-triazolo[4,3-a][1,4]diazepine as an amorphous powder.

EXAMPLE 6

To a solution of 3 g of 4-(2-chlorophenyl)-2-(1-hydroxyethyl)-ethyl-9-methyl-6H-thieno [3,2-f][1,2,4]triazolo[4,3-a][1,4]diazepine dissolved in 50 ml of pyridine is added 2.2 g of 4-chlorobenzoyl chloride under ice-cooling and then stirred for 2 hours. After completion of the reaction, the mixture is concentrated under reduced pressure and the residue is dissolved in 50 ml of ethyl acetate. The solution is washed with 5% aqueous sodium hydrogencarbonate solution and sodium chloride solution and dried over anhydrous magnesium sulfate. After filtering off, the filtrate is concentrated under reduced pressure and the oily residue is subjected to chromatography on silica gel and eluted with chloroform-methanol (100:1-100:3). The objective fraction is concentrated under reduced pressure followed by crystallization from isopropyl ether to give 0.53 g of 2-(1-(4-chlorobenzoyl)oxyethyl)-4-(2-chlorophenyl)-9-methyl-6H-thieno[3,2-f][1,2,4]triazolo[4,3a][1,4]diazepine as crystals, melting at 177°-180° C.

EXAMPLE 7

To a solution of 3.6 g of 4-(2-chlorophenyl)-2-(1-hydroxyethyl)-9-methyl-6H-thieno[3,2-f][1,2,4]triazolo[4,3-a][1,4]diazepine dissolved in 30 ml of pyridine is added 2 g of 4-phenylpropionyl chloride under ice-cooling and then stirred for 2 hours. After completion of the reaction, the mixture is concentrated under reduced pressure and the residue is dissolved in 50 ml of ethyl acetate. The solution is washed with 5% aqueous sodium hydrogencarbonate solution and sodium chloride solution and dried over anhydrous magnesium sulfate. After filtering off, the filtrate is concentrated under reduced pressure and the oily residue is subjected to chromatography on silica gel and eluted with chloroform-methanol (100:1-100:3). The objective fraction is concentrated under reduced pressure to give 0.5 g of 2-(1-(2-phenylpropionyl)-oxyethyl)-4-(2-chlorophenyl)-9-methyl-6 H-thieno[3,2-f][1,2,4]triazolo[4,3-a][1,4]diazepine as an amorphous powder, melting at 67°-75° C.

EXAMPLE 8

To a solution of 3.6 g of 4-(2-chlorophenyl)-2-(1-hydroxyethyl)-9-methyl-6H-thieno [3,2-f][1,2,4]triazolo[4,3a][1,4]diazepine dissolved in 50 ml of pyridine is added 2 g of 4-cinnamoyl chloride under ice-cooling and then stirred for 2 hours. After completion of the reaction, the mixture is concentrated under reduced pressure and the residue is dissolved in 50 ml of ethyl acetate. The solution is washed with 5% aqueous sodium hydrogencarbonate solution and sodium chloride solution and dried over anhydrous magnesium sulfate. After filtering off, the filtrate is concentrated under reduced pressure and the oily residue is subjected to chromatography on silica gel and eluted with chloroform-methanol (100:1–100:3). The objective fraction is concentrated under reduced pressure followed by crystallization from ethyl acetate to give 0.4 g of 2-(1-cinnamoyloxyethyl)-4-(2-chloro-phenyl)-9-methyl-6H-thieno[ 3,2-f][1,2,4]triazolo[4,3-a][1,4]diazepine as crystals, melting at 122°–125° C.

EXAMPLE 9

To a solution of 3 g of 4-(2-chlorophenyl)-2-(1-hydroxyethyl)-9-methyl-6H-thieno [3,2-f][1,2,4]triazolo[4,3-a][1,4]diazepine dissolved in 30 ml of pyridine is added 2.2 g of tridecanoyl chloride under ice-cooling and then stirred for 2 hours. After completion of the reaction, the mixture is concentrated under reduced pressure and the residue is dissolved in 50 ml of ethyl acetate. The solution is washed with 5% aqueous sodium hydrogencarbonate solution and sodium chloride solution and dried over anhydrous magnesium sulfate. After filtering off, the filtrate is concentrated under reduced pressure and the oily residue is subjected to chromatography on silica gel and eluted with chloroform-methanol (100:1–100:3). The objective fraction is concentrated under reduced pressure followed by crystallization from isopropyl ether to give 0.5 g of 4-(2-chlorophenyl)-2-(1-tridecanoyl-oxyethyl)-9-methyl-6H-thieno[3,2-f][1,2,4]triazolo[4,3a][1,4]diazepine as crystals, melting at 78 - 79° C.

EXAMPLE 10

To a solution of 0.9 g of 4-(2-chlorophenyl)-2-(1-hydroxyethyl)-9-methyl-6H-thieno[3,2-f][1,2,4]triazolo[4,3a][1,4]diazepine dissolved in 20 ml of pyridine is added 0.6 g of 4-octyloxybenzoyl chloride under ice-cooling and then stirred for 2 hours. After concentrating under reduced pressure, the residue is dissolved in 50 ml of ethyl acetate, the solution is washed with 5% aqueous sodium hydrogencarbonate solution and sodium chloride solution and dried over anhydrous magnesium sulfate. After filtering off, the filtrate is concentrated under reduced pressure and the oily residue is subjected to chromatography on silica gel and eluted with chloroform-methanol (100:1–100:3). The objective fraction is concentrated under reduced pressure to give 0.1 g of 4-(2-chlorophenyl) 9-methyl-2-(1-(4-octyloxybenzoyl)oxyethyl)-6H-thieno[3,2-f][1,2,4]triazolo[4,3-a][1,4]diazepine as an amorphous powder, melting at 56°–61° C.

EXAMPLE 11

To a solution of 0.9 g of 4-(2-chlorophenyl)-2-(1-hydroxyethyl)-9-methyl-6H-thieno[3,2-f][1,2,4]triazolo[4,3a][1,4]diazepine dissolved in 20 ml of pyridine is added 0.7 g of 4-(4-phenylbutyloxy)benzoyl chloride under ice-cooling and then stirred for 2 hours. After completion of the reaction, the mixture is concentrated under reduced pressure and the residue is dissolved in 50 ml of ethyl acetate. The solution is washed with 5% aqueous sodium hydrogencarbonate solution and sodium chloride solution and dried over anhydrous magnesium sulfate. After filtering off, the filtrate is concentrated under reduced pressure and the oily residue is subjected to chromatography on silica gel and eluted with chloroform-methanol (100:1–100:3). The objective fraction is concentrated under reduced pressure to give 0.3 g of 4-(2-chlorophenyl) -9-methyl-2-(1-(4-(4-phenylbutyloxy)benzoyl)-oxyethyl)-6-H-thieno[3,2-f][1,2,4]triazolo[4,3-a][1,4]diazepine as an amorphous powder, melting at 80°–90° C.

EXAMPLE 12

To a solution of 1 g of 4-(2-chlorophenyl)-2-(1-hydroxyethyl)-9-methyl-6H-thieno [3,2-f][1,2,4]triazolo[4,3-a][1,4]diazepine dissolved in 20 ml of pyridine is added 1 ml of acetic anhydride under ice-cooling and then stirred overnight. After completion of the reaction, the mixture is concentrated under reduced pressure and the residue is dissolved in 30 ml of ethyl acetate. The solution is washed with 5% aqueous sodium hydrogencarbonate solution and sodium chloride solution and dried over anhydrous magnesium sulfate. After filtering off, the filtrate is concentrated under reduced pressure and the oily residue is subjected to chromatography on silica gel and eluted with chloroform-methanol (100:1–100:3). The objective fraction is concentrated under reduced pressure to give 0.9 g of 2-(1-acetoxyethyl)-4-(2-chlorophenyl)-9-methyl-6H-thieno[3,2-f][1,2,4]triazolo[4,3-a]- [1,4]diazepine.hydrochloride melting at 168°–175° C.

EXAMPLE 13

To a solution of 1 g of 4-(2-chlorophenyl)-2-(1-hydroxyethyl)-9-methyl-6H-thieno[3,2-f][1,2,4]triazolo[4,3-a][1,4]diazepine dissolved in 20 ml of pyridine is added 0.4 g of benzoyl chloride under ice-cooling and then stirred overnight. After completion of the reaction, the mixture is concentrated under reduced pressure and the residue is dissolved in 30 ml of ethyl acetate. The solution is washed with 5% aqueous sodium hydrogencarbonate solution and sodium chloride solution and dried over anhydrous magnesium sulfate. After filtering off, the filtrate is concentrated under reduced pressure and the oily residue is subjected to chromatography on silica gel and eluted with chloroform-methanol (100:1–100:3). The objective fraction is concentrated under reduced pressure to give 0.4 g of 2-(1-benzoyloxyethyl)-4-(2-chlorophenyl)-9-methyl-6H-thieno[3,2-f][1,2,4]triazolo[4,3-a][1,4]diazepine.hydrochloride, melting at 180°14 193° C. with decomposition.

EXAMPLE 14

To a solution of 3 g of 4-(2-chlorophenyl)-2-(1-hydroxyethyl)-9-methyl-6H-thieno[3,2-f][1,2,4]triazolo[4,3-a][1,4]diazepine dissolved in 30 ml of pyridine is added 1 g of pivaloyl chloride under ice-cooling and then stirred overnight. After completion of the reaction, the mixture is concentrated under reduced pressure and the residue is dissolved in 30 ml of ethyl acetate. The solution is washed with 5% aqueous sodium hydrogencarbonate solution and sodium chloride solution and dried over anhydrous magnesium sulfate.

After filtering off, the filtrate is concentrated under reduced pressure and the residue is subjected to chromatography on silica gel and eluted with chloroform-methanol (100:1-100:3). The objective fraction is concentrated under reduced pressure followed by crystallization from ligroinethyl acetate to give 1.1 g of 4-(2-chlorophenyl)-9-methyl-2(1-pivaloyloxyethyl)-6H-thieno[3,2-f][1,2,4]triazolo[4,3-a][1,4]diazepine as crystals, melting at 148°-151° C.

The following compounds can be prepared in a similar manner as mentioned in above examples.

* 4-(2-chlorophenyl)-9-methyl-2-pentadecanoyloxy-6H-thieno[3,2-f][1,2,4]triazolo[4,3-a][1,4]diazepine as light yellowish vitreous solid
* 4-(2-chlorophenyl)-9-methyl-2-(1-(2-(4-phenoxyphenyl)-propionyl)oxyethyl)-6H-thieno[3,2-f][1,2,4]triazolo[4,3-a][1,4]diazepine.
* 4-(2-chlorophenyl)-9-methyl-2-(1-(2-(2-phenylbenzothiazol5-yl)propionyl)oxyethyl)-6 [3,2-f][1,2,4]triazolo[4,3-a][1,4]diazepine.
* 4-(2-chlorophenyl)-9-methyl-2-(1-(2-(2-fluoro-4-biphenylyl)propionyl) oxymethyl)-6H-thieno[3,2-f][1,2,4]triazolo[4,3-a][1,4]diazepine.
* 4-(2-chlorophenyl)-2-(1-(2-(6-methoxynaphtalen-2-yl)-propionyl)oxy) methyl-9-methyl-6H-thieno[3,2-f][1,2,4]triazolo[4,3-a][1,4]diazepine.
* 2-(1-(2-(4-cyclohexylphenyl)propionyl)oxyethyl)-4-(2-chlorophenyl)-9-methyl-6H-thieno[3,2-f][1,2,4]triazolo[4,3a][1,4]diazepine.
* 4-(2-chlorophenyl)-9-methyl-2-(1-(2-(4-(2-pyridylamino)-phenyl)propionyl)[oxyethyl)-6H-thieno[3,2-f][1,2,4]triazolo 4,3-a][1,4]diazepine.
* 2-(1-(2-(3-benzoylphenyl)propionyl)oxyethyl)-4-(2-chloro-phenyl)propionyl) -9-methyl-6H-thieno[3,2-f][1,2,4]triazolo[4,3-a][1,4]-diazepine.
* 2-(1-(2-(6-chloro-9H-carbazol-2-yl)propionyl)oxypropyl)-4-(2-chlorophenyl)-9-methyl-6H-thieno[3,2-f][1,2,4]triazolo-[4,3-a][1,4]-diazepine.
2-(1-(2-(5H-[1]benzopyrano[2,3-b]pyridin-7-yl)propionyl)-oxyethyl)-4-(2-chlorophenyl)-9-methyl-6H-thieno[3,2-f][1,2,4]triazolo[4,3-a][1,4]-diazepine.
* 2-(1-(1-(4-chlorobenzoyl)-5-methoxy-2-methylindol-3-acetyl)oxyethyl)-4-(2-chlorophenyl)-9-methyl-6H-thieno[3,2f][1,2,4]triazolo[4,3-a][1,4]-diazepine.

Formulation examples of the compounds of the present invention for drugs can be illustrated as follows:

FORMULATION EXAMPLE 1: TABLETS

1 Part of the compound of the present invention, 30 parts of lactose, 40 parts of crystalline cellulose and 5 parts of corn starch are mixed well in a kneader and then kneaded with a binder prepared by 2 parts of corn starch. The wet mass is passed through a 16 mesh sieve and then dried in an oven at 50° C. The dry granule is forced through a 24 mesh sieve. The obtained poder is mixed well with 10 parts of corn starch, 13 parts of crystalline cellulose and 9 parts of talc and compressed into tablets to give 110 mg of tablets.

FORMULATION EXAMPLE 2:1% POWDER

1 Part of the compound of the present invention and 90 parts of lactose are mixed well in a kneader and then kneaded with a binder prepared by a suitable amount of methyl cellulose. The wet mass is passed through a 16 mesh sieve and then dried in an oven at 50° C. The dry granule is forced through a 32 mesh sieve and mixed well with a suitable amount of silicon dioxide to give 1% of powder.

Although the present invention has been adequately discussed in the foregoing specification and examples included therein, one readily recognizes that various changes and modifications may be made without departing from the spirit and scope thereof.

We claim:

1. An ester-substituted thienotriazolodiazepine compound of the formula:

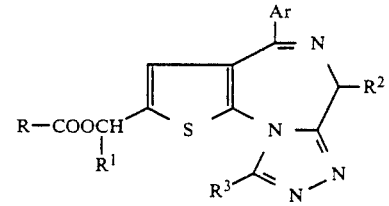

wherein Ar is phenyl substituted by one halogen, $R^1$ is alkyl having 1 to 4 carbon atoms, $R^2$ is hydrogen or alkyl having 1 to 4 carbon atoms, $R^3$ is alkyl having 1 to 4 carbon atoms, R is 4-isobutyl-α-methylbenzyl, and pharmaceutically acceptable salts thereof.

2. The compound claim 1 which is 2-(1-(2-(4-isobutylphenyl)propionyl)pxyethyl)-4-(2-chlorophenyl)-9-methyl-6H-thieno[3,2-f][1,2,4]triazolo[4,3-a][1,4,]diazepine.

* * * * *